United States Patent [19]

Auron et al.

[11] Patent Number: 5,001,057

[45] Date of Patent: Mar. 19, 1991

[54] TRUNCATED HUMAN IL-1 CDNA SEQUENCES WHICH ENCODE BIOLOGICALLY-ACTIVE HUMAN IL-1 PROTEINS

[75] Inventors: Philip E. Auron, Framingham; Andrew C. Webb, Wellesley; Lee Gehrke, Framingham; Charles A. Dinarello, Boston; Lanny J. Rosenwasser, Weston; Alexander Rich, Cambridge; Sheldon M. Wolff, Wellesley, all of Mass.

[73] Assignees: New England Medical Center; Tufts College, both of Boston; Wellesley College, Wellesley; MIT, Cambridge, all of Mass.

[21] Appl. No.: 184,211

[22] Filed: Apr. 21, 1988

Related U.S. Application Data

[60] Division of Ser. No. 700,374, Feb. 11, 1985, Pat. No. 4,762,914, which is a continuation-in-part of Ser. No. 611,669, May 18, 1984, abandoned.

[51] Int. Cl.$^5$ .................... C12P 21/00; C12N 1/20; C12N 15/00; C07H 21/04
[52] U.S. Cl. .................... 435/69.52; 435/252.3; 435/320.1; 536/27
[58] Field of Search ............... 435/69.52, 172.3, 252.3, 435/252.31–252.35, 320; 536/27

[56] References Cited

U.S. PATENT DOCUMENTS 4,766,069  8/1988  Auron et al. .................... 435/69.52

OTHER PUBLICATIONS

Pharmacia P-L Biochemicals 1984 Product Reference Guide, p. 26.
Auron et al.; Proc. Natl. Acad. Sci. U.S.A., 81:7907, (1984).
Roberts et al.; Proc. Natl. Acad. Sci. U.S.A., 76:760, (1979).

*Primary Examiner*—James Martinell
*Attorney, Agent, or Firm*—Saliwanchik & Saliwanchik

[57] ABSTRACT

The subject invention concerns truncated human IL-1 cDNA sequences which encode biologically-active novel human IL-1 proteins. These truncated human IL-1 cDNA sequences can be obtained by genetic engineering procedures using a clone of human IL-1 cDNA, having the accession number NRRL B-15770, as a starting material. The truncated human IL-1 cDNA sequences of the subject invention are contained in specified plasmids whose constructions are described in detail. Biologically-active human IL-1 proteins are useful to induce the production of IL-2 by activated T-cells. They also act on B-cells and NK-cells.

7 Claims, No Drawings

TRUNCATED HUMAN IL-1 CDNA SEQUENCES WHICH ENCODE BIOLOGICALLY-ACTIVE HUMAN IL-1 PROTEINS

CROSS REFERENCE TO A RELATED APPLICATION

This application is a divisional of U.S. Ser. No. 700,374, filed Feb. 11, 1985, now U.S. Pat. No. 4,762,914, which is a continuation-in-part of U.S. Ser. No. 611,669, filed May. 18, 1984, now abandoned.

BACKGROUND OF THE INVENTION

Interleukin 1 (IL-1) is a protein produced by activated mononuclear phagocytes and performs a broad range of functions in host defense and immunoregulation (Dinarello, C. A. [1984] New England J. Med. 311, 1413–1418). Recently it has been demonstrated that Il-1 is first synthesized as a precursor molecule of about 270 amino acids in length (approximately 30,000 molecular weight) which is proteolytically processed into a smaller molecule (approximately 18,000 molecular weight) which possesses full biological activity (Auron, P. E., Webb, A. C., Rosenwasser, L. J., Mucci, S. F., Rich, A., Wolff, S. M., and Dinarello, C. A. [1984] Proc. Natl. Acad. Sci. U.S.A. 81. The sequence for human IL-1 is shown in Chart A.

BRIEF SUMMARY OF THE INVENTION

The subject invention concerns truncated human IL-1 cDNA sequences which encode biologically-active human IL-1 proteins. These truncated cDNA sequences, and novel biologically-active human IL-1 proteins obtained therefrom, can be obtained by genetic engineering procedures using a clone containing the entire human IL-1 cDNA sequence as starting material. Specifically, with reference to Chart A, the nucleotide sequence located between residues 534 and 893 encode biologically-active IL-1 proteins. Within this range are two regions which encode biologically-active IL-1 proteins; i.e., (1) the nucleotide sequence located between residues 534 and 710, and (2) the nucleotide sequence located between residues 711 and 893.

DETAILED DESCRIPTION OF THE INVENTION

The subject invention, advantageously, provides novel biologically-active human IL-1 proteins through use of novel truncated human IL-1 cDNA sequences. As disclosed above, the entire human IL-1 cDNA sequence is shown in Chart A. This sequence is the starting material for the preparation of the novel clones of the subject invention, as disclosed hereinafter in the Examples.

Clone (plasmid)pcD-415, which contains the cDNA for human monocyte IL-1, was deposited in an E. coli HB101 host in the permanent collection of the Northern Regional Research Laboratory, U.S. Department of Agriculture, Peoria, Ill., U.S.A., on Apr. 27, 1984. The culture was assigned the accession number NRRL B-15770 by the repository. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

Recombinant plasmid pcD-415 can be isolated from its E. coli HB101 host by well-known procedures, e.g., using cleared lysate-isopycnic density gradient procedures, and the like.

Unlimited amounts of nucleic acid comprising nucleotide sequences coding for truncated human IL-1 can be made by the cloned human IL-1 cDNA of the subject invention. Further, the IL-1 proteins produced by the cloned cDNA of the subject invention can be used to induce the production of IL-2 by activating T-cells—IL-2 stimulates the T-cells to proliferate. As reported in Science, 221, 1362–1364, "Researchers from NIAID and the Food and Drug Administration (FDA), using a test tube assay, have recently found that interleukin-2 improved the function of T-cells from six AIDS patients" (p. 1362). In summary, the novel biologically-active human IL-1 proteins obtained via the cloned truncated human IL-1 cDNA sequences of the subject invention can be used in the same manner as native human IL-1.

The following examples are illustrative of the process and products of the subject invention but are not to be construed as limiting. All percentages are by weight and all solvent mixture proportions are by volume unless otherwise noted.

EXAMPLE 1

Construction of a Plasmid Containing Truncated Human IL-1 cDNA That Codes for Proteins Corresponding to the DNA Sequences Located Between Nucleotide Positions 87 Through 677, and Positions 1355 Through 1396 Shown in Chart A The IL-1 cDNA sequence (Chart A) contains three unique restriction endonuclease digestion sites that can be used to construct plasmids containing specific deletions aimed at isolating essential domains of IL-1. Proceeding 5' to 3' in the directional sense of protein coding by the cDNA, these three sites are located respectively named and positioned as follows: Hind III (pos. 483); Pvu II (pos. 678); and Xmn I (pos. 1355) (Note: all restriction endonuclease sites presented here are referenced to the location of the first nucleotide on the 3' side of scission as read along the protein coding "sense" strand of the cDNA). In addition a unique Pst I restriction site located upstream from the cDNA sequence (pos. −16) can also be used.

The first plasmid construction deletes all IL-1 cDNA nucleotide sequence between the Pvu II and Xmn I sites, described above, and is as follows: Plasmid pL1, as described by H. Okayama and P. Berg (1983) Molec. Cell. Biol. 3:280–289, and which can be purchased from Pharmacia (Piscataway, N.J.), is digested completely with Xmn I and Hind III restriction endonucleases. Three products which result can be resolved by agarose gel electrophoresis. These products are approximately 518, 782, and 1544 base pairs in length. The 518 base pair fragment is isolated from the agarose gel using standard techniques. Another plasmid, e.g., pUC-8 (Messing, J. and Vieira, J. [1982] Gene 19:269–276), which can be purchased from Pharmacia, is used as a source of a DNA fragment which can be used as a linker segment to attach the Pst I restriction site located at one end of the 518 base pair fragment to a Hind III site which will be described below. pUC-8 contains a polycloning site with adjacent Pst I and Hind III sites and can be substituted for by other similar DNAs such as pUC-9 or M13mp8 or M13mp9 double stranded replicative forms. These DNAs can be purchased from Pharmacia. The pUC-8 plasmid is digested with Pst I and mixed with the 518 base pair fragment derived from pL1. The two fragments are ligated by T4 DNA ligase under conditions of excess pUC-8. Two products which result represent two different ligated orientations of the 518 fragment with respect to the linearized pUC-8. The two different orientations cannot easily be isolated from each other since each possesses the same molecular size (approximately 3660 base pairs). Isolation is accomplished by first digesting the 3660 base pair DNA mixture with Hind III endonuclease which causes the original mixture to be fragmented into 4 products of approximately 3650, 3140, 528, and 10 base pairs in length. These products can readily be resolved by standard agarose gel electrophoresis and the 528 base pair, pL1-derived, fragment (which now possess Hind III cohesive ends) is isolated.

The original human IL-1 cDNA plasmid (pcD-415), contained in the *E. coli* HB101 host, is isolated using standard plasmid preparation procedures. This plasmid is digested with both Pvu II and Xmn I restriction endonucleases to yield three products which are resolvable by agarose gel electrophoresis (approximate sizes are 675, 1633, and 2379 base pairs). The 1633 and 2379 base pair fragments are isolated from the gel and ligated in the presence of T4 DNA ligase to the pL1-derived, 528 base-pair fragment, described above. Two different plasmid constructs result, one of which has the proper orientation for the DNA fragments. The correct construct can readily be isolated by taking advantage of the fact that the ampicillin resistance gene contained within the pcD-415 plasmid will be properly reassembled only in the plasmid construction containing the desired IL-1 cDNA fragment orientation. Therefore *E. coli* HB101 cells transformed with the mixture containing both plasmids will only yield viable *E. coli* cells containing the proper construct when the cells are grown in the presence of ampicillin. From these cells the final construct (which is referred to as pcD-415ΔPvu/Xmn) can be isolated using standard plasmid isolation procedures. This plasmid contains truncated human IL-1 cDNA that codes for a protein corresponding to the DNA sequence located between nucleotide positions 87 through 677 and positions 1355 through 1396 shown in Chart A.

EXAMPLE 2

Construction of a Plasmid Containing Truncated Human IL-1-cDNA that Codes for a Protein Corresponding to the DNA Sequence Located Between Nucleotide Positions 492 Through 893 Shown in Chart A This plasmid is constructed such that all the cDNA sequence between the upstream Pst I site and the Hind III site contained within the human IL-1 sequence is deleted. The starting material is plasmid pcD-415. Plasmid pcD-415 is digested with Hind III endonuclease and the two products (approximately 1016 and 3676 base pairs) resolved by agarose gel electrophoresis. The 3676 base pair fragment is isolated from the gel and mixed with the pL1-derived, 528 base pair (Hind III cohesive-ended) fragment prepared for use in constructing pcD-415ΔPvu/Xmn in Example 1. Ligation of these DNAs by T4 ligase results in two different plasmid products which can be purified and distinguished by transformation of *E. coli* HB101 cells and restriction mapping of the isolated plasmids. A Pvu II and Pst I double digestion permits clear identification of the product. The final product with the required deletion is referred to as pcD-415ΔPst/Hin. This plasmid contains a truncated human IL-1 cDNA that codes for a protein corresponding to the DNA sequence located between nucleotide positions 492 through 893 shown in Chart A.

EXAMPLE 3

Construction of a Plasmid Containing Truncated Human IL-1 cDNA that Codes for Proteins Corresponding to the DNA Sequence Located Between Nucleotide Positions 492 Through 677 and Positions 1355 Through 1396 Shown in Chart A.

This construction is a combination of both deletions described above located within a single plasmid. The pcD-415ΔPst/Hin plasmid, described above, is digested with Pvu II and Xmn I to yield three agarose gel resolvable products (approximately 675, 1150, and 2379 base pairs). The 1150 and 2379 base pair fragments are isolated and ligated to yield two possible products which can be resolved in a fashion analogous to that described in Example 1 by selection of transformed *E. coli* HB101 in the presence of ampicillin. The final product with the required deletions is referred to as pcD-415ΔPst/Hin-ΔPvu/Xho. This plasmid contains a truncated human IL-1 cDNA that codes for proteins corresponding to the DNA sequence located between nucleotide positions 492 through 677 and positions 1355 through 1396 shown in Chart A.

The cDNA transcript can be obtained from the clones in essentially pure form by standard art methods. For example, the cDNA transcript can be clipped from a plasmid by a BamHI-Pst I double-digestion (Okayama, H. and Berg, P. [1983] Molec. Cell. Biol. 3:280–289) and isolated by standard procedures. The essentially pure cDNA thus obtained can be used for subcloning into a different transfer vector.

As is well known in the art, the amino acid sequence of a protein, e.g., the IL-1 proteins of the invention, is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATH | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Try) | TGG |
| Alanine (Ala) | GCL | Arginine (Arg) | WGZ |
| Tyrosine (Tyr) | TAK | Glycine (Gly) | GGL |
| Termination Signal | TAJ | | |
| Termination signal | TGA | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A = adenine
G = guanine
C = cytosine
T - thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T
J = A or G
K = T or C
L = A, T, C or G
M = A, C or T The above shows that the novel amino acid sequences of the human IL-1 proteins of the subject invention can be prepared by nucleotide sequences other than those disclosed herein. Functionally equivalent nucleotide sequences encoding the novel amino acid sequences of these human IL-1 proteins, or fragments thereof having IL-1 activity, can be prepared by known synthetic procedures. Accordingly, the subject invention includes such functionally equivalent nucleotide sequences.

Thus the scope of the subject invention includes not only the specific nucleotide sequences depicted herein, but also all equivalent nucleotide sequences coding for molecules with substantially the same human IL-1 biological activity. The term "equivalent" is being used in its ordinary patent usage here as denoting a nucleotide sequence which performs substantially as the nucleotide sequence identified herein to produce molecules with substantially the same human IL-1 biological activity in essentially the same kind of hosts. Within this definition are subfragments which have human IL-1 biological activity.

It is well within the skill of those in the genetic engineering art to use the nucleotide sequences encoding human IL-1 activity of the subject invention to produce human IL-1 proteins via microbial processes. Fusing the sequences into an expression vector and transforming or transfecting into hosts, either eukaryotic (yeast or mammalian cells) or prokaryotic (bacterial cells), are standard procedures used in producing other well-known proteins, e.g., insulin, interferons, human growth hormone, and the like. Similar procedures, or obvious modifications thereof, can be employed to prepare human IL-1 proteins by microbial means or mammalian tissue-culture technology in accord with the subject invention.

The nucleotide sequences obtained from IL-1 clone pCD-415 also can be prepared by a "gene machine" by procedures well known in the art. This is possible because of the disclosure of the nucleotide sequence. However, it is generally recognized in the art at this time that obtention of the desired nucleotide sequence from a clone, e.g., pCD-415, is the most expedient way to practice an invention such as disclosed and claimed herein.

The restriction enzymes disclosed can be purchased from Bethesda Research Laboratories, Gaithersburg, Md., or New England Biolabs, Beverly, Mass. The enzymes are used according to the instructions provided by the supplier.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, e.g., *E. coli* cells, prepare plasmid DNA, electrophorese proteins, and sequence DNA.

CHART A

```
ACAAACCTTTTCGAGGCAAAAGGCAAAAAA
        10          20          30

GGCTGCTCTGGGATTCTCTTCAGCCAATCT
        40          50          60

METALA
TCAATGCTCAAGTGTCTGAAGCAGCCATGG
        70          80          90

GLUVALPROLYS LEUALASER GLUMETMET
CAGAAGTACCTAAGCTCGCCAGTGAAATGA
        100         110         120

ALATYRTYRSER GLYASNGLUASP ASP LEU
TGGCTTATTACAGTGGCAATGAGGATGACT
        130         140         150

PHEPHEGLU ALAASP GLYPROLYS GLNMET
TGTTCTTTGAAGCTGATGGCCCTAAACAGA
        160         170         180

LYS CYS SER PHEGLNASP LEUASP LEUCYS
TGAAGTGCTCCTTCCAGGACCTGGACCTCT
        190         200         210

PROLEUASP GLYGLYILE GLNLEUARGILE
GCCCTCTGGATGGCGGCATCCAGCTACGAA
        220         230         240

SERASP HIS HIS TYRSER LYS GLYPHEARG
TCTCCGACCACCACTACAGCAAGGGCTTCA
        250         260         270

GLNALAALASER VALVALVALALAMETASP
GGCAGGCCGCGTCAGTTGTTGTGGCCATGG
        280         290         300

LYS LEUARGLYS METLEUVALPROCYS PRO
ACAAGCTGAGGAAGATGCTGGTTCCCTGCC
        310         320         330

GLNTHRPHEGLNGLU ASNASP LEUSER THR
CACAGACCTTCCAGGAGAATGACCTGAGCA
        340         350         360

PHEPHEPROPHEILE PHEGLUGLUGLUPRO
CCTTCTTTCCCTTCATCTTTGAAGAAGAAC
        370         380         390

ILE PHEPHEASP THRTRP ASP ASNGLU ALA
CTATCTTCTTCGACACATGGGATAACGAGG
        400         410         420

TYRVALHIS ASP ALAPROVALARGSER LEU
CTTATGTGCACGATGCACCTGTACGATCAC
        430         440         450

ASNCYS THRLEUARGASP SER GLNGLNLYS
TGAACTGCACGCTCCGGGACTCACAGCAAA
        460         470         480

SER LEUVALMETSERGLYPROTYRGLULEU
AAAGCTTGGTGATGTCTGGTCCATATGAAC
        490         500         510
```

-continued
CHART A

```
LYS ALA LEU HIS LEU GLN GLY GLN ASP MET
TGAAAGCTCTCCACCTCCAGGGACAGGATA
      520       530       540

GLU GLN GLN VAL VAL PHE SER MET SER PHE
TGGAGCAACAAGTGGTGTTCTCCATGTCCT
      550       560       570

VAL GLN GLY LY GLU GLU SER ASN ASP LYS ILE
TTGTACAAGGAGAAGAAAGTAATGACAAAA
      580       590       600

PRO VAL ALA LEU GLY LEU LYS GLU LYS ASN
TACCTGTGGCCTTGGGCCTCAAGGAAAAGA
      610       620       630

LEU TYR LEU SER CYS VAL LEU LYS ASP ASP
ATCTGTACCTGTCCTGCGTGTTGAAAGATG
      640       650       660

LYS PRO THR LEU GLN LEU GLU SER VAL ASP
ATAAGCCCACTCTACAGCTGGAGAGTGTAG
      670       680       690

PRO LYS ASN TYR PRO LYS LYS LYS MET GLU
ATCCCAAAAATTACCCAAAGAAGAAGATGG
      700       710       720

LYS ARG PHE VAL PHE ASN LYS ILE GLU ILE
AAAAGCGATTTGTCTTCAACAAGATAGAAA
      730       740       750

ASN ASN LYS LEU GLU PHE GLU SER ALA GLN
TCAATAACAAGCTGGAATTTGAGTCTGCCC
      760       770       780

PHE PRO ASN TRP TYR ILE SER THR SER GLN
AGTTCCCCAACTGGTACATCAGCACCTCTC
      790       800       810

ALA GLU ASN MET PRO VAL PHE LEU GLY GLY
AAGCAGAAAACATGCCCGTCTTCCTGGGAG
      820       830       840

THR LYS GLY GLY GLN ASP ILE THR ASP PHE
GGACCAAAGGCGGCCAGGATATAACTGACT
      850       860       870

THR MET GLN PHE VAL SER SER ***
TCACCATGCAATTTGTGTCTTCCTAAAGAG
      880       890       900

AGCTGTACCCAGAGAGTCCTGTGCTGAATG
      910       920       930

TGGACTCAATCCCTAGGGCTGGCAGAAAGG
      940       950       960

GAACAGAAAGGTTTTTGAGTACGGCTATAG
      970       980       990

CCTGGACTTTCCTGTTGTCTACACCAATGC
     1000      1010      1020

CCAACTGCCTGCCTTAGGGTAGTGCTAAGA
     1030      1040      1050

GGATCTCCTGTCCATCAGCCAGGACAGTCA
     1060      1070      1080

GCTCTCTCCTTTCAGGGCCAATCCCAGCCC
     1090      1100      1110

TTTTGTTGAGCCAGGCCTCTCTCACCTCTC
     1120      1130      1140

CTACTCACTTAAAGCCCGCCTGACAGAAAC
     1150      1160      1170

CAGGCCACATTTTGGTTCTAAGAAACCCTC
     1180      1190      1200

CTCTGTCATTCGCTCCCACATTCTGATGAG
     1210      1220      1230

CAACCGCTTCCCTATTTATTTATTTATTTG
     1240      1250      1260

TTTGTTTGTTTTGATTCATTGGTCTAATTT
     1270      1280      1290

ATTCAAAGGGGGCAAGAAGTAGCAGTGTCT
     1300      1310      1320

GTAAAAGAGCCTAGTTTTTAATAGCTATGC
     1330      1340      1350

AATCAATTCAATTTGGACTGGTGTGCTCTC
     1360      1370      1380

TTTAAATCAAGTCCTTTAATTAAGACTGAA
     1390      1400      1410

AATATATAAGCTCAGATTATTTAAATGGGA
     1420      1430      1440

ATATTTATAAATGAGCAAATATCATACTGT
     1450      1460      1470

TCAATGGTTCTCAAATAAACTTCACTAAAA
     1480      1490      1500

AAAAAAA
```

We claim:

1. A recombinant DNA cloning vehicle comprising cDNA coding for truncated human IL-1 protein of the amino acid sequence:

MET ALA GLU VAL PRO LYS LEU ALA SER GLU MET
MET ALA TYR TYR SER GLY ASN GLU ASP ASP LEU
PHE PHE GLU ALA ASP GLY PRO LYS GLN MET LYS
CYS SER PHE GLN ASP LEU ASP LEU CYS PRO LEU
ASP GLY GLY ILE GLN LEU ARG ILE SER ASP HIS
HIS TYR SER LYS GLY PHE ARG GLN ALA ALA SER
VAL VAL VAL ALA MET ASP LYS LEU ARG LYS MET
LEU VAL PRO CYS PRO GLN THR PHE GLN GLU ASN
ASP LEU SER THR PHE PHE PRO PHE ILE PHE GLU
GLU GLU PRO ILE PHE PHE ASP THR TRP ASP ASN
GLU ALA TYR VAL HIS ASP ALA PRO VAL ARG SER
LEU ASN CYS THR LEU ARG ASP SER GLN GLN LYS
SER LEU VAL MET SER GLY PRO TYR GLU LEU LYS
ALA LEU HIS LEU GLN GLY GLN ASP MET GLU GLN
GLN VAL VAL PHE SER MET SER PHE VAL GLN GLY
GLU GLU SER ASN ASP LYS ILE PRO VAL ALA LEU
GLY LEU LYS GLU LYS ASN LEU TYR LEU SER CYS
VAL LEU LYS ASP ASP LYS PRO THR GLN ASN SER
ILE TRP THR GLY VAL LEU SER LEU ASN GLN VAL
LEU.

2. A process for preparing a truncated human IL-1 protein, as defined in claim 1, which comprises culturing a microbe hosting the cloning vehicle pcD-415ΔPvu/Xmn and recovering the protein.

3. A recombinant DNA cloning vehicle comprising cDNA coding for the amino acid sequence:

MET SER GLY PRO TYR GLU LEU LYS ALA LEU HIS
LEU GLN GLY GLN ASP MET GLU GLN GLN VAL VAL
PHE SER MET SER PHE VAL GLN GLY GLU GLU SER
ASN ASP LYS ILE PRO VAL ALA LEU GLY LEU LYS
GLU LYS ASN LEU TYR LEU SER CYS VAL LEU LYS
ASP ASP LYS PRO THR LEU GLN ASN SER ILE TRP

THR GLY VAL LEU SER LEU ASN GLN VAL LEU.

4. The recombinant plasmid pcD-415ΔPvu/Xmn.

5. cDNA coding for a truncated human IL-1 protein having the sequence

MET SER GLY PRO TYR GLU LEU LYS ALA LEU HIS
LEU GLN GLY GLN ASP MET GLU GLN GLN VAL VAL
PHE SER MET SER PHE VAL GLN GLY GLU GLU SER
ASN ASP LYS ILE PRO VAL ALA LEU GLY LEU LYS
GLU LYS ASN LEU TYR LEU SER CYS VAL LEU LYS
ASP ASP LYS PRO THR LEU GLN ASN SER ILE TRP
THR GLY VAL LEU SER LEU ASN GLN VAL LEU.

6. Bacteria transformed by the recombinant plasmid pcD-415ΔPvu/Xmn.

7. cDNA coding for a truncated human IL-1 protein having the sequence

MET ALA GLU VAL PRO LYS LEU ALA SER GLU MET
MET ALA TYR TYR SER GLY ASN GLU ASP ASP LEU
PHE PHE GLU ALA ASP GLY PRO LYS GLN MET LYS
CYS SER PHE GLN ASP LEU ASP LEU CYS PRO LEU
ASP GLY GLY ILE GLN LEU ARG ILE SER ASP HIS HIS
TYR SER LYS GLY PHE ARG GLN ALA ALA SER VAL
VAL VAL ALA MET ASP LYS LEU ARG LYS MET LEU
VAL PRO CYS PRO GLN THR PHE GLN GLU ASN ASP
LEU SER THR PHE PHE PRO PHE ILE PHE GLU GLU
GLU PRO ILE PHE PHE ASP THR TRP ASP ASN GLU
ALA TYR VAL HIS ASP ALA PRO VAL ARG SER LEU
ASN CYS THR LEU ARG ASP SER GLN GLN LYS SER
LEU VAL MET SER GLY PRO TYR GLU LEU LYS ALA
LEU HIS LEU GLN GLY GLN ASP MET GLU GLN GLN
VAL VAL PHE SER MET SER PHE VAL GLN GLY GLU
GLU SER ASN ASP LYS ILE PRO VAL ALA LEU GLY
LEU LYS GLU LYS ASN LEU TYR LEU SER CYS VAL
LEU LYS ASP ASP LYS PRO THR LEU GLN ASN SER ILE
TRP THR GLY VAL LEU SER LEU ASN GLN VAL LEU.
LEU GLN ASN SER ILE TRP THR GLY VAL
LEU SER LEU ASN GLN VAL LEU.

\* \* \* \* \*

UNITED STATES PATENT AND TRADEMARK OFFICE
CERTIFICATE OF CORRECTION

PATENT NO.   : 5,001,057

DATED        : March 19, 1991

INVENTOR(S)  : Philip E. Auron, Andrew C. Webb, Lee Gehrke, Charles A. Dinarello, Lanny J. Rosenwasser, Alexander Rich and Sheldon M. Wolff It is certified that error appears in the above-identified patent and that said Letters Patent is hereby corrected as shown below:

Column 8    line 53: After "LYS PRO THR" insert --LEU--.

Column 10   lines 18-19: Delete these lines.

Signed and Sealed this

Fifth Day of January, 1993

Attest:

DOUGLAS B. COMER

Attesting Officer        Acting Commissioner of Patents and Trademarks